United States Patent [19]
Ausonio et al.

[11] Patent Number: 6,162,947
[45] Date of Patent: Dec. 19, 2000

[54] PROCESS FOR THE PREPARATION OF 4-CARBOXY-5, 8,11-TRIS (CARBOXYMETHYL)-PHENYL-2-OXA-5, 8 11-TRIAZATRIDECAN

[75] Inventors: Marina Ausonio; Carlo Distaso; Giuseppe Gerardo Elia; Alessandro Lesignoli; Rodolfo Piva; Carlo Secchi; Carlo Felice Viscardi, all of Milan, Italy

[73] Assignee: Dibra S.p.A., Milano, Italy

[21] Appl. No.: 09/349,449

[22] Filed: Jul. 8, 1999

[30] Foreign Application Priority Data

Oct. 7, 1998 [IT] Italy ................... MI9801583

[51] Int. Cl.[7] ................ Z07C 229/28; Z07C 59/48
[52] U.S. Cl. ........................ 562/448; 562/470
[58] Field of Search ...................... 562/448, 470

[56] References Cited

U.S. PATENT DOCUMENTS 2,820,816  1/1958  Anspon .
5,182,370  1/1993  Felder et al. .

FOREIGN PATENT DOCUMENTS 230893  8/1987  European Pat. Off. ...... C07C 101/26

OTHER PUBLICATIONS

Aime et al Inorganic Chemistry, vol. 31, No. 6, Mar. 1992 pp. 1100–1103 XP002120082 "Synthesis and NMRD Studies of $GD^{3+}$ Complexes of Macrocyclic Polyamino Polycarboxyilic Ligands Bearing . . . "1992.

Grassman et al Chemische Berichte vol. 91, 1958, pp 538–541, XP002127665 "Darstellung und Peptidsynthetische Verwendung von O–Benzyl–serin".

Grassman et al., Chem. Ber., 1958, 91, pp. 538, 1958.

*Primary Examiner*—Deborah Carr
*Assistant Examiner*—Brian J. Davis
*Attorney, Agent, or Firm*—Nixon & Vanderhye

[57] ABSTRACT

A novel a process for the preparation of the chelating agent of formula (I)

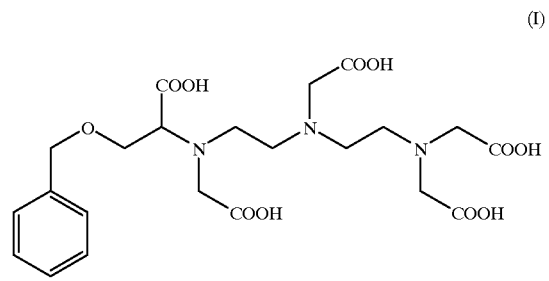

4-carboxy-5,8,11-tris(carboxymethyl)-1-phenyl-2-oxa-5,8, 11-triazatridecan-13-oic acid, commonly named BOPTA.

40 Claims, No Drawings

PROCESS FOR THE PREPARATION OF 4-CARBOXY-5, 8,11-TRIS (CARBOXYMETHYL)-PHENYL-2-OXA-5, 8 11-TRIAZATRIDECAN

The present invention relates to a novel process for the preparation of the chelating agent of formula (I), 4-carboxy-5,8,11-tris(carboxymethyl)-1-phenyl-2-oxa-5,8,11-triazatridecan-13-oic acid, commonly named BOPTA.

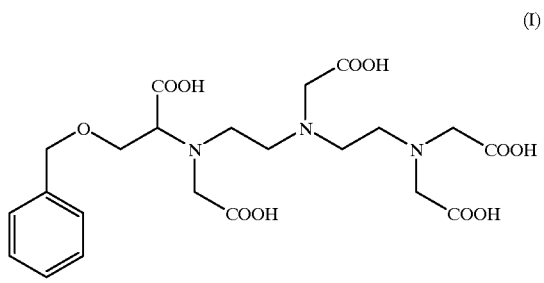

Complexes of chelating agents with specific suitable metals are already used as contrast agents in the following diagnostic techniques: X-ray imaging, nuclear magnetic resonance imaging (M.R.I.) and scintigraphy.

In particular, magnetic resonance imaging is a renowned powerful diagnostic procedure used in medical practice (Stark, D. D., Bradley, W. G., Jr., Eds. "Magnetic Resonance Imaging" The C. V. Mosby Company, St. Louis, Mo. (USA), 1988), which mainly makes use of paramagnetic pharmaceutical compositions, preferably containing chelated complexes of bi- or trivalent paramagnetic metal ions with aminopolycarboxylic acids and/or their derivatives or analogues.

Some of them are at present in clinical use as M.R.I. contrast agents (Gd-DTPA, N-methylglucamine salt of gadolinium complex with diethylenetriaminopentaacetic acid, MAGNEVIST®, Schering; Gd-DOTA, N-methylglucamine salt of gadolinium complex with 1,4,7, 10-tetraazacyclododecan-1,4,7,10-tetracetic acid, DOTAREM®, Guerbet).

The contrast agents listed above and on the market are designed for a wholly general use. In fact, after administration the M.R.I. contrast agent is distributed in the extracellular spaces in different parts of the body prior to being excreted. In this sense they behave in a similar manner to iodine compounds used in X ray medical diagnosis.

At present, the medical profession increasingly requires contrast agents that are also aimed at specific organs, which cannot be well visualized by means of the usual products already commercially available. In particular, there is a need for contrast agents for the liver, an organ which is particularly prone to tumoral metastases, which are almost always carcinomatous metastases. Among the M.R.I. contrast agents under development the complex salt Gd-BOPTA-Dimeg, has turned out to be particularly suitable, in addition to its general use, also in the imaging of hepatic tissue, in that it is excreted also through the bile route (see e.g. Vittadini G., et al., Invest. Radiol., (1990), 25(Suppl. 1), S59–S60).

The synthesis of the chelating agent of formula (I) was first disclosed in EP 230893 and further described in the paper: Uggeri F., et al., Inorg. Chem., 1995, 34(3), 633–42, always starting from diethylenetriamine.

The synthetic scheme disclosed in the two references is the following:

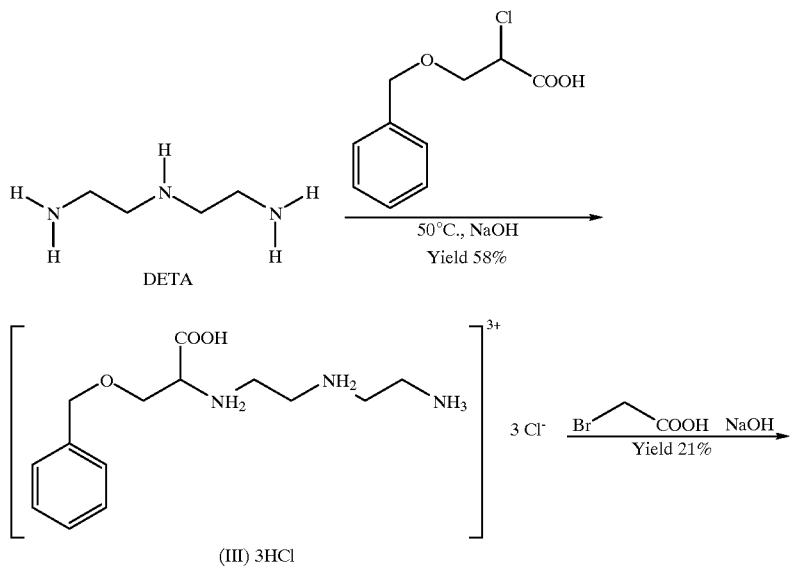

-continued

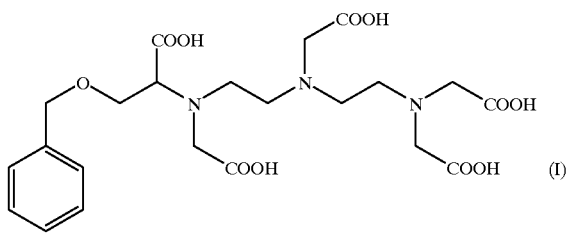
(I)

and it comprises the selective monoalkylation of a primary nitrogen of diethylenetriamine (DETA) (in a strong excess, about 13 times to the stoichiometric) with 2-chloro-3-phenylmethoxy propionic acid in the presence of water at a temperature of 50° C.: the intermediate, N-[2-[(2-aminoethyl)amino]ethyl]-O-(phenylmethyl)serine of formula (III) is then recovered as trihydrochloride salt.

In the second step, the obtained intermediate is fully carboxymethylated with bromoacetic acid in water at pH 10 to give the compound of formula (I).

The problems observed with this type of process were the following:

- the preparation of 2-chloro-3-(phenylmethoxy)propionic acid analogously to the synthesis of the bromine derivative described in Grassman et al., (Chem. Ber., 1958, 91, 538), involves the final hydrolysis of the corresponding ethyl ester, previously distilled, which has an unsatisfactory purity (HPLC assay: 90–92%) that affects the process to the final compound (I);
- the amount of hydrochloric acid necessary to displace all the compound from the anionic resin is remarkable and its concentration under heat gives rise to a side-product of formula (IV), corresponding to the 6-membered lactam between the acidic group and the adjacent amino group.

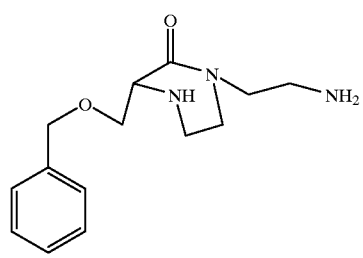
(IV)

The formation of compound (IV) had already been observed during the preparation of compound (I), as a secondary product from the condensation reaction, which had been recovered from the aqueous eluate containing the excess DETA on the anionic resin column in a 10% percentage. The subsequent concentration of the acid eluates had to be carried out at controlled temperature to avoid formation of the above cited product (40° C.).

The industrial application of this process on an industrial scale would therefore require concentrating at controlled temperature such high amounts of acid eluates from preparations on a large scale, as to make said process unworkable: in a 110 mol scale experiment, at the end of the thermal concentration about 70% of the product had been converted to lactam (IV).

Moreover, a problem that had not been evidenced in the cited references is the purity of the resulting product which should necessarily fulfil the requirements (for example Federal Register, vol. 61, no. 3, Jan. 4, 1996) and the guide-lines demanded by the various regulatory authorities (for example ICH, Specifications test procedures and acceptance criteria for new drug substances and new drug procedures, Chem. Subst., Jul. 16, 1996), also considering the intrinsic danger involved by this type of products due to the parenteral administration and the administered dose. Those requirements can thus be summarized: purity of the compound (I) higher than or equal to 99%, present impurities lower than or equal to 1%, the single impurities being not above 0.1%.

It should be clearly understood that, in view of a commercialisation of this novel M.R.I. contrast agent, a synthesis giving the above mentioned yields would be wholly unsatisfactory from the industrial point of view, thus requiring a novel process for the preparation of compound (I).

It is therefore the object of the invention a novel process for the preparation of compound (I) comprising the steps represented in the following Scheme 1:

Scheme 1

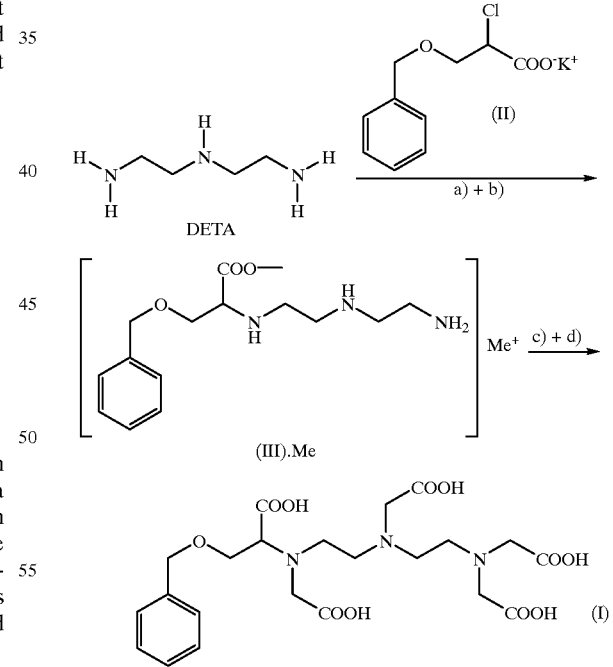

in which in step a) 2-chloro-3-(phenylmethoxy)propionic acid potassium salt of formula (II) is reacted in water, at 50–70° C. and at pH of about 12 by addition of an alkali or alkaline-earth metal (Me) oxide or hydroxide, with a DETA excess 6–7 times the molar amount of (II), to give the aqueous solution of the novel compound, N-[2-[(2- aminoethyl)amino]ethyl]-O-(phenylmethyl)serine salt of formula (III) with the corresponding metal cation;

in step b) the solution from step a) is fed to a strong anionic resin in the OH— form, then is eluted with water and with a NaCl/HCl solution, then is fed to a polystyrene-based macroporous adsorbing resin, desalted by nanofiltration, and thermally evaporated to reach a final concentration of 20–50% (w/w) in compound (III) which can be used as such directly in step c);

in step c) bromoacetic acid is slowly aided to the solution from step b), at pH 11–12, to give the aqueous solution of crude compound (I);

in step d) the solution of compound (I) from step c) is purified and compound (I), which meets the purity quality specifications, is isolated.

The process of the invention allowed to solve the problems involved in the prior art process, in that:

the use of the 2-chloro-3-[(phenylmethoxy)methyl] propionic acid potassium salt allows to isolate a product with much higher purity (HPLC impurities ≦1%).

compound (III) is no longer recovered as trihydrochloride, but as alkali or alkaline-earth metal salt, preferably as sodium salt

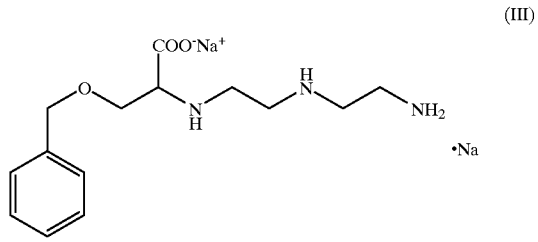

(III)

and the reaction is carried out at controlled basic pH.

This modification to the procedure surprisingly reduces the side-formation of compound (IV) which is formed in much lower percentages than with the prior art, i.e. 0.8–3%.

Furthermore, according to the process of the invention, the thermal concentration of an aqueous acidic solution is no longer necessary for the recovery of compound (III): most water is in fact removed at room temperature by nanofiltration and the thermal concentration, in order to remove the poor amount of residual water, is carried out at alkali pH, at which the product is surprisingly more stable.

The introduction of purification steps b) and c), according to the procedure of the present invention, allows one to obtain a final product which always conforms with the pharmacopoeia specifications in a quite reproducible way.

Step a) comprises the reaction of compound (II) in a DETA excess, the optimum ratio being 1:5/1:8, therefore markedly lower than in the above references. The overall yield of this step can be up to 80%.

It is preferable to operate in the presence of a water amount ranging from 0.1 to 0.3 g per gram of DETA to start the reaction.

During the addition of water to the reagents cold mixture, the reaction temperature spontaneously increases to 50° C. as a consequence of the exothermal dissolution of DETA in water.

When temperature exceeds 50° C., the reaction starts, and temperature further increases due to the reaction exothermy and is adjusted to about 60° C. to complete the reaction.

It has surprisingly been found that the lactamization rate decreases as the pH and the water amount increase.

It has been found that the presence of water and pH of about 12 substantially inhibit the secondary reaction of formation of lactam (IV), whereas by-products related to the substitution and elimination induced by OH⁻ ions do not significantly increase. Inorganic bases which can be used are alkali or alkaline-earth metal hydroxides, preferably sodium and potassium hydroxides.

Particularly preferred is sodium hydroxide, and the solution used is preferably 30% by weight.

The basic solution is added in amounts of about 0.9 mols of OH⁻ per mol of compound (II).

The solution is then cooled to 25° C., diluted with water and subjected to the purification step b).

In step b) the solution is first percolated onto a strong anionic resin in OH⁻ form, analogously to what described in the references above. The anionic resins employable are selected from the group consisting of strong resins, preferably with trimethylammonium or triethylammonium functional groups.

The product and the anionic impurities present in the reaction mixture are adsorbed by the resin, whereas DETA, non-anionic impurities and cations (sodium, potassium) are eluted with water.

In this step the side-product of formula (IV), which anyway does not exceed 3% by weight, can be removed.

The next step of the process is the elution of the desired product from the resin with an aqueous solution containing sodium chloride (about 0.5 N) and hydrochloric acid (about 0.3 N). This mixture is adjusted to saturate the residual OH⁻ sites without excess of acid, which would transform the product into compound (IV): the exchange reaction on the resin can thus be represented

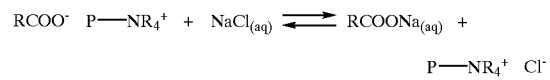

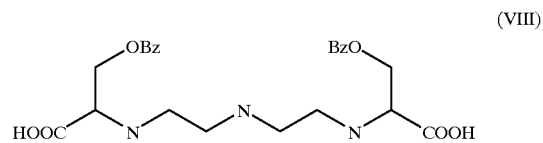

The substantially neutral or poorly alkaline eluate at the column outlet can be adjusted to pH 11.5 and fed to a macroporous polystyrene-based adsorbing resin, which removes the lipophilic impurities of the product, among which the compound of formula (VIII).

(VIII)

Suitable resins for this purpose are selected from the group consisting of: macroporous polystyrene-matrix resins with cross-linking degree from 8 to 80%, for example Bayer OC 1062 and Diaion HP 21.

The eluate from the adsorbing resin, which contains compound (III) together with sodium chloride, is finally concentrated and desalted by nanofiltration.

The pH is then adjusted to 12 to prevent the lactamization and the final solution is thermally concentrated at about 50° C. to a 20–50%, preferably 40% (w/w), final concentration and pH is adjusted to 12.5 with NaOH.

The resulting aqueous solution of the compound (III) sodium salt can be kept below 25° C., analyzed and used directly in the following step.

In step c) the solution of the compound (III) sodium salt from step b) is subjected to carboxymethylation reaction with bromoacetic acid at 55° C., at basic pH of 11–12, in a ratio of about 6.7 mols of bromoacetic acid per mol of compound (III).

These conditions allow to complete the reaction while avoiding an excessive formation of quaternary ammonium salts.

The 80% w/w bromoacetic acid solution is dropped into the solution of the compound (III) sodium salt in about 4 hours; pH is kept alkaline by simultaneous addition of an inorganic base, in particular 30% NaOH, which salifies the bromoacetic acid and the bromide ions (Br⁻) formed in the reaction.

Compared with the procedures described in the above references, the process of the invention reverses the order of addition of the reactives, while keeping basic pH throughout the reaction. These modifications resulted in better reproducibility, less critical addition times of the reactives and higher yield due to the better selectivity.

Furthermore, the gradual addition of bromoacetic acid allows a better control of the reaction exothermy, which in its turn allows to operate at higher concentrations.

pH is kept at about 11.5 thus avoiding the formation of quaternary ammonium salts of the tricarboxymethylated compound (III), which formation at low pH is competitive with that of compound (I). Higher pH values require large amounts of bromoacetic acid due to the competition of OH⁻ in the substitution of bromine.

The reaction is completed at about 55° C. in about 5 hours. the pH of the solution is adjusted to about 5 by addition of a 34% hydrochloric acid solution (w/w) to give the aqueous solution containing the crude compound (I).

In the literature references cited above, a procedure for the purification and recovery of the product is reported, consisting of two steps:

percolation of the resulting solution onto a strong acidic cation exchanger, elution with an ammonium hydroxide solution, then concentration and acidification with hydrochloric acid;

slow separation of the amorphous solid of the residue obtained from water to give compound (I).

As a matter of fact, both steps turned out to be unsuitable for the production on an industrial scale. The volume of cationic resin necessary to fix the product is very high; moreover the time necessary for the elution step is remarkable, the productivity of the step being therefore very low.

Furthermore, a remarkable volume of ammonia eluate should be thermally concentrated. In the separation step of the solid an oily viscous phase first separates, which solidifies in time to form crusts which have subsequently to be transformed mechanically.

An alternative method for the purification and recovery of compound (I) which could be more favourable for the industrial development has therefore been studied.

The process of the invention substantially differs from the above cited one in the recovery and purification procedures, which comprise the following additional steps in step d):

d.1. additional elution of the final solution of compound (I) from step b) on chromatographic resin d.2. concentration and desalting by nanofiltration;

d.3. addition of acetone, as insolubilizer, in the crystallization step of compound (I).

The purification method of the process of the invention allows to obtain a final product, in the crystalline form, having the same or better quality than that obtainable with the prior art procedure.

The operative procedure of the invention therefore eliminates the problems connected with the use of cations exchanger bed and provides compound (I) in the crystalline form which is easy to centrifuge and suitable for drying even in a dynamic drier and on the industrial scale.

In step d.1. the solution containing the crude compound (I) is percolated onto a chromatographic resin to remove the lipophilic impurities, the product being eluted with water.

The elution of the final solution onto a limited amount of resin attains a dramatic reduction of the side-products, which are difficult to remove through only crystallization.

Suitable chromatographic resins are selected from the group consisting of: macroporous polystyrene-based resins with cross-linking higher than 60%, such as Rohm & Haas XAD 1600 o 1600 T, Bayer OC 1064, Diaion Relite SP 800.

Step d.2. consists in the nanofiltration to concentrate the eluate and desalt and purify it from low molecular side-products, such as glycolic acid, bromoacetic acid and benzyl alcohol.

The retentate solution is thermally concentrated under reduced pressure, at 40–60° C., to obtain an aqueous solution of the crude compound (I).

Afterwards this is acidified to pH 2.0 at 45° C.; and step d.3., i.e. the crystallization step of compound (I), starts.

It has surprisingly been found that the addition of acetone in suitable concentration, pH and temperature conditions allows to obtain compound (I) in the crystalline form, which after separation from mother liquors, yields a humid precipitate which is very friable and easy-to-dry.

It is important, in particular, to avoid pH values lower than those indicated: this could induce the precipitation of the product in a sticky, difficult-to-stir form, thus jeopardizing the purifying effect of the crystallization.

Conversely, pH values higher than those prescribed would result in a strong decrease in the isolation yield.

The weight ratio anhydrous compound (I) to acetone to be added to the acidified aqueous solution is=1:1.5.

Lower acetone percentages in the solvent will negatively affect the yield in crude compound (I), whereas higher amount (up to 27%) are useless.

Acetone and crystals of compound (I) are added at about 41° C. and the crystallization mixture is kept under stirring at the same temperature for at least 18 h; then it is slowly cooled in about 5 h at 25° C. and cooled to 17° C. for a further 24 h. The solid obtained by centrifugation is washed with a 10% (w/w) acetone aqueous solution.

Step d.3. can also be repeated when the resulting product does not satisfies the purity specifications required. In particular, three crystallization steps are preferably carried out.

It is a further object of the invention the preparation of 2-chloro-3-(phenylmethoxy)propionic acid potassium salt comprising the steps represented in the following Scheme 2, without isolating the intermediates:

Scheme 2

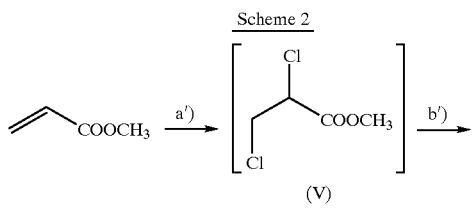

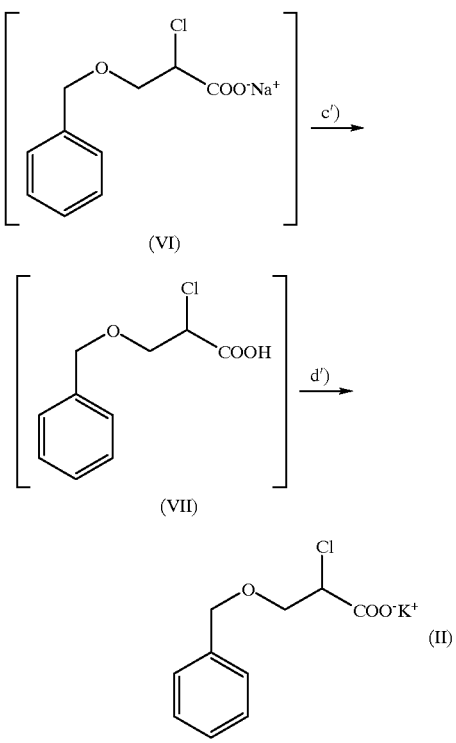

in which in step a') methyl acrylate is chlorinated in the presence of catalytic amounts of dimethylformamide to give 2,3-dichloropropionic acid methyl ester of formula (V);

in step b') the solution from step a') is first added, without exceeding 10° C., to the sodium benzylate anhydrous solution, prepared by reaction between benzyl alcohol and sodium hydroxide, subsequently dehydrated by azeotropical distillation, then treated with sodium hydroxide, to give an organic phase containing 2-chloro-3-(phenylmethoxy)propionic acid sodium salt of formula (VI);

in step c') the organic phase from step b') is acidified with hydrochloric acid to give an aqueous solution of 2-chloro-3-(phenylmethoxy)propionic acid of formula (VII);

in step d') the acidic aqueous phase from step c') is neutralized with potassium hydroxide and the 2-chloro-(phenylmethoxy)propionic acid potassium salt of formula (II) is recovered by crystallization after addition of sec-butanol.

In step a') methyl acrylate is reacted with the stoichiometric amount of chlorine in the presence of dimethylformamide as catalyst in an amount of about 3% in mols. Chlorine is bubbled through the reaction solution of methyl acrylate and DMF at room temperature: chlorine not immediately reacted saturates the reactor top thus promoting the reagents exchange. The internal pressure is kept to a maximum of 0.1 bar above the atmospheric pressure by dosing the chlorine flow. The reaction is exothermic and the temperature is controlled at about 45° C. by cooling with water. The reaction is considered completed when the stoichiometric amount of chlorine supplied has been absorbed.

Lower temperatures have been found to slow down the chlorine adsorption kinetics.

The use of dimethylformamide as catalyst is mandatory: the tests carried out without catalyst have not been completed due to the exceedingly long times for chlorine adsorption.

Sodium benzylate is prepared conventionally by reacting benzyl alcohol and 30% NaOH. The solution is dehydrated by distilling under vacuum the heterogeneous azeotrope water/benzyl alcohol and then humid benzyl alcohol to pressure lower than 20 mbars and at a temperature of 110° C.: (residual water content below 0.4% w/w by Karl Fischer).

An amount of sodium benzylate solution equivalent to 120–140% on the stoichiometric to methyl acrylate is cooled to 5° C. and then, without exceeding 10° C., the solution from step a') is dropped therein. At the end the mixture is stirred for 15–30 minutes at 5–10° C., then a 30% NaOH amount, equivalent to 80–100% on the stoichiometric amount to methyl acrylate, is dropped therein without exceeding 15° C.

Cooling is stopped and water is added. After stirring, the mixture is left to stand until complete, marked separation of the two phases.

The mainly aqueous lower phase is discarded. The benzyl upper phase, containing 2-chloro-3-benzyloxypropionic acid sodium salt, is added with a sodium chloride solution. After the usual work up, the marked and completed separation of two phases is obtained, the lower acidic aqueous phase being discarded.

In step c') the organic phase is acidified to pH 2.5 with 34% HCl w/w, stirring and at a temperature not above 20° C.; stirring is interrupted and the mixture is left to stand until two phases separate markedly and completely.

In step d') the organic phase containing 2-chloro-3-benzyloxy-propionic acid is adjusted to pH 7.2 by addition of 50% KOH.

The formation of the potassium salt is exothermic and the temperature is conveniently kept below 35° C. with circulating water.

The solution containing compound (II) is partially dehydrated by distillation at a partial pressure of about 20 mbars and at a temperature not above 55° C. The water content should range from 4 to 10% w/w. Lower or higher values should be corrected by addition of water or continuing distillation.

2-Butanol is added at 50° C., slowly cooling to crystallize the desired product. The resulting humid product is dried at 60° C. and under reduced pressure, preferably at 20 mbars.

Yields starting from methyl acrylate are around 60–70%.

The following examples illustrate the best experimental conditions to carry out the process of the invention.

Experimental Section

EXAMPLE 1

Isolation of 1-(aminoethyl)-2-oxo-3-[(phenylmethoxy) methyl]-piperazine prepared according to the procedure described in EP 230893 and Uggeri F., et al, Inorg. Chem., 1995, 34 (3), 633–42.

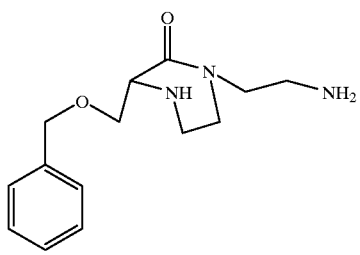

(IV)

42.9 g of 2-chloro-3-[(phenylmethoxy)methyl]propionic acid (0.2 mol) are reacted with 268.2 g of DETA (2.58 mol) at 50° C. in 400 mL of water, and the solution is percolated on an Amberlite® IRA 400 column (1880 mL), then washed with water and the basic phase is collected. This basic phase contains the excess DETA and the desired product. The solution is neutralized with 37% HCl (465 mL) and evaporated to small volume, then acidified to pH 2 with 37% HCl (365 mL). After concentration to about 800 g and standing overnight at room temperature, the solution is filtered, washed with absolute ethanol and dried to obtain DETA trihydrochloride (173.5 g, 0.81 mol). Mother liquors are concentrated to about 450 g, taken up with the washing ethanol used above and 800 mL of absolute ethanol, then, after two hours at 0–5° C., filtered, washed with absolute ethanol and dried to obtain DETA trihydrochloride (313.4 g, 1.47 mol). Crystallization waters and washings are combined and evaporated to a residue, which is taken up with ethyl ether, triturated, filtered and dried, to obtain a mixture of DETA trihydrochloride and the desired product. The mixture is then dissolved in 80 mL of water and percolated on a XAD 2 700 mL column, washing with water. Fractions of about 70 mL are collected and subjected to TLC ($R_f$= 0.38). The fractions containing the desired product are collected and evaporated to a residue, which is crystallized from absolute ethanol. The precipitate is filtered, washed with absolute ethanol and dried to obtain 7.1 g of the desired product (0.021 mol).

Yield: 10.5% m.p.: 163° C.

HPLC assay: 95.8% (in area %)

| | Elementary Analysis | | | |
|---|---|---|---|---|
| | C | H | Cl | N |
| % calc. | 50.0 | 6.89 | 21.08 | 12.50 |
| % found | 49.64 | 6.73 | 21.24 | 12.72 |

TLC: Stationary phase: silica gel plate 60F 254 Merck

Eluent: $CHCl_3/AcOH/H_2O$=5/5/1

Detection: 1% $KMnO_4$ in 1N NaOH Rf=0.38

$^1$H-NMR, $^{13}$C-NMR, IR and MS spectra are consistent with the indicated structure.

EXAMPLE 2

Preparation of compound (III) on an industrial scale according to the procedure described in the literature cited in Example 1

The reaction is carried out according to the conventional procedure, using 23.7 kg (110 mol) of 2-chloro-3-(phenylmethoxy)propionic acid with 149 kg (1430 mol) of DETA in 250 L of water. After percolating the final solution on an Amberlite® IRA 400 column (1000 L, OH$^-$), and eluting the product with 1N HCl, an aqueous solution made acidic by hydrochloric acid is evaporated to a concentration of about 1 mol/L, equivalent to 2200 L.

The solution is concentrated to small volume in about 15 hours at 50° C. The resulting residue is taken up into absolute ethanol. Upon cooling, a product precipitates which is filtered and washed with absolute ethanol. Crystallization from absolute ethanol and subsequent drying yield 24 kg of the desired product (71.5 mol).

Yield: 65%

The chemical-physical characteristics are in agreement with those cited in Example 1.

EXAMPLE 3

2-Chloro-3-(phenylmethoxy)propionic acid

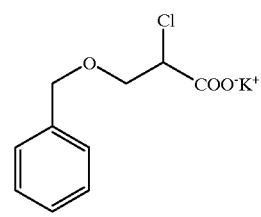

(II)

A) Preparation of 1,2-dichloro-propionic acid methyl ester 3.23 kg of methyl acrylate and 0.096 kg of dimethylformamide are loaded in a reactor under vacuum. After completion of the operation, the reactor is isolated, kept under reduced pressure and connected with a chlorine cylinder equipped with a flow control valve.

Chlorine is bubbled through the reaction solution at room temperature. The inner pressure is checked to a maximum of 0.1 bar above atmospheric pressure. The reaction is exothermic and temperature is kept at 45° C. by cooling with water. The reaction is considered completed when 2.66 kg of chlorine have been supplied and absorbed. The operation takes place in about 2 hours and 30 minutes. The amount of chlorine supplied is controlled by weighing the cylinder.

B) Preparation of Sodium Benzylate in Solution of Benzyl Alcohol 34.5 kg of benzyl alcohol and 6.7 kg of 30% NaOH are loaded in a steel reactor equipped with stirrer and fitted for distillation under vacuum. The solution is dried, distilling under vacuum the heterogeneous water/benzyl alcohol azeotrope and then the humid benzyl alcohol at a pressure lower than 20 mbars and at 110° C.

C) Preparation of 2-chloro-3-(phenylmethoxy)propionic acid potassium salt

The sodium benzylate solution is placed in a stainless steel reactor equipped with stirrer and cooling jacket, cooled at 5° C., then, without exceeding 10° C., 1,2-dichloropropionic acid methyl ester is dropped therein. The addition time depends on the ability of the plant to keep temperature within the predetermined limits; addition time should not exceed 4 hours, as in this case remarkable amounts of undesired side-products form. After completion of the addition the mixture is stirred for 15–30 minutes at 5–10° C.; then 4.4 kg of 30% NaOH are added dropwise, without exceeding 15° C. Cooling is stopped and a suitable amount of water is added. Stirring is continued for 30 minutes, then is stopped and the reaction mixture is left to stand until completion and marked separation of two phases. The mainly aqueous lower phase is discarded. The benzylic upper phase containing 2-chloro-3-benzyloxypropionic acid sodium salt is added with a NaCl water solution to promote the separation of the phases and the lower aqueous one is discarded. The organic phase is stirred below 20° C. and adjusted to pH 2.5–3.0 with 34% HCl w/w. The phases are separated and the lower aqueous acidic phase is discarded, water is added and the phases are separated again, removing the upper aqueous phase. The organic phase containing 2-chloro-3-benzyloxy-propionic acid is adjusted to pH 7.2 with 50% KOH, the reaction is exothermic and temperature is kept below 35° C. with circulating water. The solution containing the desired compound is in part dried by distillation at partial pressure of about 20 mbars and at temperature not above 55° C. After that, water content is determined by Karl Fischer and adjusted to a value equivalent to 5%.

The resulting solution is added with 54 kg of 2-butanol at 50° C., and left to spontaneously cool under stirring. Once reached 40° C. the solution is seeded: most product precipitates between 38 and 30° C. When temperature reaches 25° C., the solution is cooled to 15° C. with circulating water, keeping this temperature for 1 hour, then is centrifuged and washed with 2-butanol to obtain the humid product, which is dried for 10 hours at 60° C. and at partial pressure of 20 mbars. 5.8 kg of dry product are obtained.

Yield: 66% (on the starting methyl acrylate mols)
K.F.: 3.0% (w/w)
HPLC assay: 100.0% (ext. st.) HPLC impurities: 0.15% (% area)
Column LiChrospher 100 RP8 (5 mm, 25 cm×4 mm)
Mobile phase
A) Aqueous solution containing 1.2 mL/L of 85% $H_3PO_4$ (w/w)
B) Acetonitrile

| Gradient | linear t (min) | % B (v/v) |
|---|---|---|
| | 0 | 40 |
| | 15 | 60 |
| | 25 | 60 |
| | 26 | 40 |
| | 36 | 40 |

Flow: 1 mL/min
Temperature 30° C.
Detection UV, 215 nm

The chemical-physical analytical characteristics are consistent with those indicated in the paper by Aime S., Inorg. Chem., 1992, 31, 1100.

EXAMPLE 4

Preparation of 1,2-dichloro-propionic acid methyl ester without DMF 34.83 g of methyl acrylate are loaded in a reactor under vacuum, connected with a chlorine cylinder equipped with flow control valve.

Chlorine is bubbled through the reaction solution at room temperature. Chlorine is absorbed very slowly. The mixture is heated to 40° C. 2 hours later, 12.5 g of chlorine have been absorbed. After a further 8 hours, 6 g more have been absorbed. During 10 h at 40° C. only 18.5 g of chlorine are absorbed equivalent to 64% on theoretical.

EXAMPLE 5

Preparation of Compound (I)

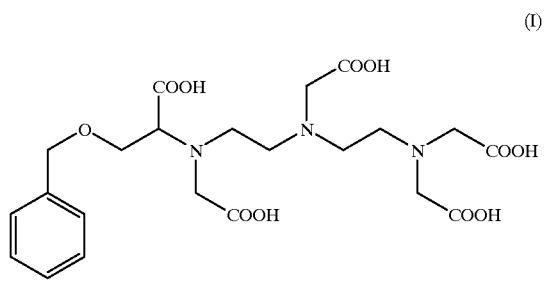

A) Preparation of the Aqueous Solution of N-[2-[(2-aminoethyl)amino]ethyl]-O-(phenylmethyl)serine sodium salt 265 kg of compound (II) (1.05 kmol) are reacted with 758 kg of DETA (7.35 kmol) in the presence of 129 kg of water; temperature spontaneously raises to 50° C. When temperature exceeds 50° C., the reaction starts, and the temperature further raises due to the reaction exothermy and is kept at about 60° C. by cooling with water. pH is kept at about 12 by addition of a 30% sodium hydroxide solution (w/w) for about 10 hours, while keeping temperature at 60° C. The solution is then cooled to 25° C., diluted with water and percolated onto 1200 L of a polystyrene-matrix strong anionic resin in OH⁻ form. The product and the anionic impurities are adsorbed by the resin, whereas DETA, non-anionic impurities and cations (sodium, potassium) are eluted with water. Afterwards, the product is eluted with an aqueous solution containing sodium chloride and hydrochloric acid, the eluate is adjusted to pH 11.5 and fed to a column containing 210 L of macroporous polystyrene adsorbing resin, which removes the most lipophilic impurities of the product.

The eluate from the adsorbing resin, containing compound (III) together with sodium chloride, is concentrated and desalted by nanofiltration, afterwards it is adjusted to pH 12 to prevent lactamization and then thermally concentrated under reduced pressure. 650 kg of a 40% solution of the desired product (w/w) are obtained (0.67 kmol, yield from compound (II) 63%).

The solution is then stored below 25° C., analyzed and used directly in the following step.

B) Preparation of Compound (I)

195.4 kg (0.20 kmol) of the solution of compound (III) sodium salt are heated to 55° C. and reacted with 136.2 kg of an 80% bromoacetic acid aqueous solution, which are added slowly. pH is kept at 11.6 with a 30% (w/w) sodium hydroxide solution. The reaction is completed in about 55° C. and at pH 11.2 in about 5 hours. The solution is then cooled to 25° C. and pH is adjusted to about 5.5 with a 34% hydrochloric acid solution (w/w). The solution containing the crude compound (I) is percolated onto a chromatographic resin (XAD 1600, 150 L) to remove the lipophilic impurities; the product is eluted with water and the eluate is concentrated and partially desalted by nanofiltration.

The retentate solution is warm concentrated under reduced pressure to obtain a crude solution having a compound (I)/water ratio of about 1/6. After that, pH is adjusted to 2.0 and temperature to 45° C.; acetone and crystals of compound (I) are added at about 41° C. The crystallization mixture is kept under stirring at the same temperature for at least 18 h; then it is slowly cooled to 25° C. in about 5 h and to 17° C. for a further 24 h.

The solid is recovered by centrifugation and washed with an 10% acetone aqueous solution (w/w), then the crude is dissolved in deionized water at about 55° C. When the dissolution is completed, the solution is cooled to about 47° C.; and the previous procedure of seeding and subsequent crystallization is repeated. The obtained solid is then dissolved again in deionized water at about 55° C. When the dissolution is completed, the solution is filtered to remove the particles, and partially evaporated to remove any traces of volatile organic impurities contained in the acetone used in the two previous crystallizations. The solution is then cooled to 47° C. and crystallized under the same conditions as defined above.

127 kg of humid crystalline product are recovered by centrifugation and dried at 35° C. and 35 mbars, to yield 68 kg of the desired product (0.121 kmol).

Yield: 60.5% from compound (II)

K.F.: 8% (w/w)

Titre : 100.1% (ext. standard.)

HPLC impurities : 0.15%

What is claimed is:

1. A process for the preparation of compound of formula (I)

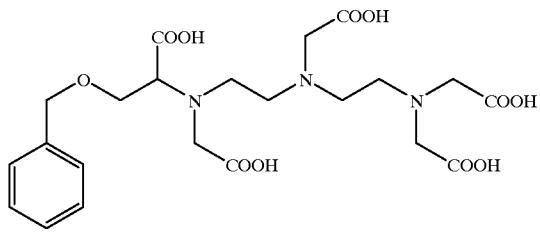

comprising the successive steps of:

(a) reacting 2-chloro-3-(phenylmethoxy)propionic acid potassium salt of formula (II)

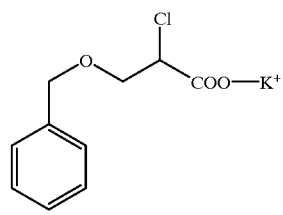

in a solution and in the presence of an alkali or alkaline-earth metal (Me) oxide or hydroxide, with diethyltriamine to give the N-[2-[(2-aminoethyl) amino]ethyl]-O-(phenylmethyl)serine salt of formula (III) with corresponding metal cation

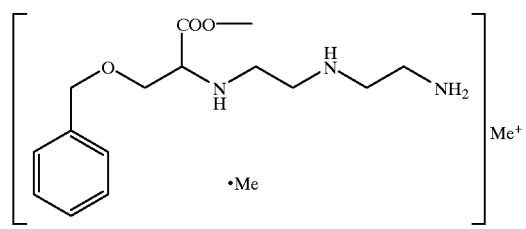

(b) purifying and concentrating the solution containing compound (III);

(c) reacting compound (III) with bromoacetic acid while maintaining a basic pH; then (d) purifying and isolating compound (I).

2. A process as claimed in claim 1, in which the reaction of step a) is carried out in water.

3. A process as claimed in claim 2, in which water is present in an amount ranging from 0.1 to 0.3 g per gram of DETA.

4. A process as claimed in claim 1, in which the reaction of step a) is carried out at a temperature of 50–70° C.

5. A process as claimed in claim 4, in which the temperature is 60° C.

6. A process as claimed in claim 1, in which in step a) the pH is kept at about 12.

7. A process as claimed in claim 6, in which the pH is kept at about 12 by addition of sodium hydroxide in an amount of about 0.9 mols of $OH^-$ per mol of compound (II).

8. A process as claimed in claim 1, in which DETA in step a) is used in an excess of 6–7 times the molar amount of (II).

9. A process as claimed in claim 1, in which the DETA to compound (II) molar ratio is from 1:5 to 1:8.

10. A process as claimed in claim 1, in which the purification of the solution containing compound (III), in step b), is carried out by treatment of the solution from step a) with a strong anionic resin in $OH^-$ form, followed by elution with water and with a NaCl/HCl solution, subsequent treatment of the eluate with a macroporous polystyrene adsorbing resin and desalting by nanofiltration.

11. A process as claimed in claim 10, in which the anionic resins are selected from strong resins having trimethylammonium and triethylammonium functional groups, the macroporous adsorbing resin is a polystyrene matrix resin with cross-linking between 8 and 80%.

12. A process as claimed in claim 1, in which the concentration of the solution containing compound (III), in step b), is carried out by thermal evaporation to reach a 20–50% w/w final concentration of compound (III).

13. A process as claimed in claim 1, in which the reaction of step c) is carried out at pH 11–12.

14. A process as claimed in claim 13, in which the pH is 11.5.

15. A process according to claim 13, in which the pH is kept constant by addition of sodium hydroxide.

16. A process as claimed in claim 1, in which the reaction of step c) is carried out at a temperature of 55° C.

17. A process as claimed in claim 1, in which the reaction of step c) is carried out at a bromoacetic acid to compound (III) molar ratio of 6.7:1.

18. A process as claimed in claim 1, in which step d) is carried out by percolation of the solution containing compound (I) on chromatographic resin, elution with water, nanofiltration, concentration of the retentate solution, acidification and crystallization by addition of acetone.

19. A process as claimed in claim 18, in which the chromatographic resin is selected from the group consisting of macroporous polystyrene resins with cross-linking higher than 60%.

20. A process as claimed in claim 18, in which the concentration of the retentate solution is carried out under reduced pressure at 40–60° C.

21. A process as claimed in claim 18, in which the acidification is carried out at pH 2.0 at 45° C.

22. A process as claimed in claim 18, in which the anhydrous compound (I) to acetone weight ratio is 1:15.

23. A process as claimed in claim 18, in which the crystallization step is repeated at least three times.

24. A process for the preparation of 2-chloro-3-(phenylmethoxy)propionic acid potassium salt (II)

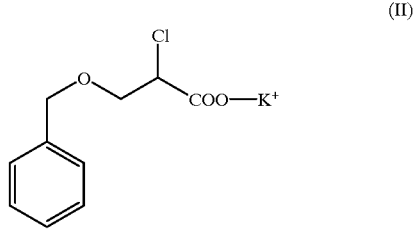

without isolating any intermediates, the process comprising the successive steps of:
(a) chlorinating methyl acrylate to give 2,3-dichloropropionic methyl ester acid;
(b) reacting 2,3-dichloropropionic methyl ester acid in an organic solvent with anhydrous sodium benzylate, and subsequently treating it with sodium hydroxide to give 2-chloro-3-(phenylmethoxy)propionic acid sodium salt in an organic phase;
(c) acidifying the organic phase from step (b) to give an aqueous solution of 2-chloro-3-(phenylmethoxy) propionic acid; and
(d) neutralizing the acidic aqueous phase of step (c) with potassium hydroxide and recovering compound (II).

25. A process as claimed in claim 24, in which step a') is effected in the presence of catalytic amounts of dimethylformamide.

26. A process as claimed in claim 25, in which the amount dimethylformamide catalyst is of about 3 mol %.

27. A process as claimed in claim 24, in which step a') is effected at a pressure up to a maximum of 0.1 bar above atmospheric pressure.

28. A process as claimed in claim 24, in which step a') is effected at a temperature of 45° C.

29. A process as claimed in claim 24, in which step b') is effected at temperatures below 10° C.

30. A process as claimed in claim 24, in which the sodium benzylate of step b') is obtained by reaction between benzyl alcohol and sodium hydroxide and subsequent dehydration by azeotropical distillation.

31. A process as claimed in claim 24, in which the sodium benzylate used in step b') is in solution with a residual water content lower than 0.4% w/w.

32. A process as claimed in claim 24, in which in step b') the sodium benzylate solution is added in an amount equivalent to 120–140% of the stoichiometric amount to methyl acrylate.

33. A process as claimed in claim 24, in which in step b') the amount of 30% by weight sodium hydroxide used is equivalent to 80–100% of the stoichiometric amount of the methyl acrylate.

34. A process as claimed in claim 24, in which the acidification of step c') is carried out with 34% w/w HCl to pH 2.5.

35. A process as claimed in claim 24, in which the neutralization of step d') is carried out by addition of 50% by weight KOH to pH 7.2.

36. A process as claimed in claim 24, in which the isolation of compound (II) of step d') is carried out by crystallization.

37. A process as claimed in claim 36, in which said isolation is carried out by partial dehydration of the solution containing compound (II) and subsequent addition of 2-butanol as a crystallization solvent.

38. A process as claimed in claim 37, in which the partial dehydration is carried out by distillation at a partial pressure of about 20 mbars and at a temperature below 55° C.

39. A process as claimed in claim 38, in which the distillation is carried out to a water content of from 4 to 10% w/w.

40. A process as claimed in claim 37, in which the addition of 2-butanol is carried out at a temperature of 50° C.

* * * * *